(12) United States Patent
Magno et al.

(10) Patent No.: US 11,207,083 B2
(45) Date of Patent: *Dec. 28, 2021

(54) INTEGRATED SUCTION AND COOLING OF ANGLED BURR

(71) Applicant: Gyrus ACMI, Inc., Southborough, MA (US)

(72) Inventors: Joey Magno, Cordova, TN (US); Saeed A. Merza, Cordova, TN (US)

(73) Assignee: Gyrus Acmi, Inc., Westborough, MA (US)

(*) Notice: Subject to any disclaimer, the term of this patent is extended or adjusted under 35 U.S.C. 154(b) by 206 days.

This patent is subject to a terminal disclaimer.

(21) Appl. No.: 16/545,569

(22) Filed: Aug. 20, 2019

(65) Prior Publication Data

US 2019/0365389 A1 Dec. 5, 2019

Related U.S. Application Data

(63) Continuation of application No. 15/464,492, filed on Mar. 21, 2017, now Pat. No. 10,413,305.

(51) Int. Cl.
*A61B 17/16* (2006.01)
*A61B 17/32* (2006.01)
(Continued)

(52) U.S. Cl.
CPC ...... *A61B 17/1644* (2013.01); *A61B 17/1615* (2013.01); *A61B 17/1631* (2013.01);
(Continued)

(58) Field of Classification Search
CPC ............ A61B 17/1613; A61B 17/1615; A61B 17/1631; A61B 17/1633; A61B 17/1642;
(Continued)

(56) References Cited

U.S. PATENT DOCUMENTS 3,937,222 A 2/1976 Banko
6,482,216 B1 11/2002 Hiblar et al.
(Continued)

FOREIGN PATENT DOCUMENTS

CN 108618826 A 10/2018
DE 297 13 897 U1 12/1998
(Continued)

OTHER PUBLICATIONS

S.S. White Technologies Inc., Retrieved Mar. 8, 2017 from http://www.swt.com/flexible-shaft.htm, 3 pages.
(Continued)

*Primary Examiner* — Eric S Gibson
(74) *Attorney, Agent, or Firm* — Schwegman Lundberg & Woessner, P.A.

(57) ABSTRACT

Disclosed herein is a surgical device. The surgical device includes a cutting burr, a flexible/deflectable shaft, an elongated fluted shaft, a sheath, and an outer tube. The cutting burr has a fluted extension. The flexible/deflectable shaft has a distal end and a proximal end, the distal end is configured to be connectable to the fluted extension of the cutting burr. The elongated fluted shaft is configured to be connectable to the proximal end of the flexible shaft. The sheath is configured to receive all or portion of the flexible shaft and the elongated fluted shaft. The outer tube is configured to receive the sheath such that there is enough space for fluid irrigation between the outer tube and the sheath.

20 Claims, 8 Drawing Sheets

(51) Int. Cl.
*A61B 17/3207* (2006.01)
*A61B 17/00* (2006.01)

(52) U.S. Cl.
CPC .. *A61B 17/1633* (2013.01); *A61B 17/320758* (2013.01); *A61B 17/32002* (2013.01); *A61B 2017/00685* (2013.01); *A61B 2017/1651* (2013.01); *A61B 2217/005* (2013.01); *A61B 2217/007* (2013.01)

(58) Field of Classification Search
CPC ............ A61B 17/1644; A61B 17/1651; A61B 17/32002; A61B 17/320758
See application file for complete search history.

(56) References Cited

U.S. PATENT DOCUMENTS

| | | | |
|---|---|---|---|
| 8,939,979 B2 | 1/2015 | Del Rio et al. | |
| 9,113,917 B2 | 8/2015 | Del Rio et al. | |
| 10,413,305 B2* | 9/2019 | Magno | A61B 17/1633 |
| 2003/0130663 A1 | 7/2003 | Walen | |
| 2005/0177168 A1 | 8/2005 | Brunnett et al. | |
| 2009/0234378 A1 | 9/2009 | Escudero | |
| 2014/0180321 A1 | 6/2014 | Dias et al. | |
| 2016/0081699 A1 | 3/2016 | Edwards | |
| 2018/0271544 A1* | 9/2018 | Magno | A61B 17/1644 |
| 2019/0365389 A1* | 12/2019 | Magno | A61B 17/1615 |

FOREIGN PATENT DOCUMENTS

| | | | |
|---|---|---|---|
| EP | 3141201 A1 | 3/2017 | |
| EP | 3378418 A1 | 9/2018 | |
| EP | 3378418 B1 | 10/2019 | |
| JP | 2016511074 A | 4/2016 | |
| JP | 6877811 B2 | 5/2021 | |
| WO | WO-01/64115 A2 | 9/2001 | |
| WO | WO-03024340 A2 | 3/2003 | |

OTHER PUBLICATIONS

Tubing PVC Class VI, 2016 Qosina Catalog, pp. 220, 221 (on one sheet), 2016.
Sinus Surgery and Transnasal Skull Base Surgery, Retrieved Mar. 20, 2017, from http://www.medtronic.com/us-en/healthcare-professionals/therapies-procedures/ear-nose-throat/sinus-surgery.html, 7 pages.
Powered Ent Instruments—ENT Systems and Handpieces, Retrieved Mar. 20, 2017, from http://www.medtronic.com/us-en/healthcare-professionals/products/ear-nose-throat/powered-ent-instruments.html, 5 pages.
Powered Ent Instruments from Medtronic, Retrieved Mar. 20, 2017, from http://www.medtronic.com/us-en/healthcare-professionals/products/ear-nose-throat/powered-ent-instruments/powered-ent-instruments.html, 5 pages.
Helicut, Retrieved Mar. 20, 2017, from http://www.smith-nephew.com/uk/products/sports-medicine/resection/blades-and-burrs/helicut/, 2 pages.
"U.S. Appl. No. 15/464,492, Non Final Office Action dated Oct. 25, 2018", 14 pgs.
"U.S. Appl. No. 15/464,492, Notice of Allowance dated May 10, 2019", 7 pgs.
"U.S. Appl. No. 15/464,492, Response filed Jan. 24, 2019 to Non Final Office Action dated Oct. 25, 2018", 8 pgs.
"European Application Serial No. 18155009.6, Extended European Search Report dated Jul. 27, 2018", 5 pgs.
"European Application Serial No. 18155009.6, Intention to Grant dated Apr. 29, 2019", 35 pgs.
"European Application Serial No. 18155009.6, Response filed Mar. 19, 2019 to Extended European Search Report dated Jul. 27, 2018", 18 pgs.
"Japanese Application Serial No. 2018-32945, Notification of Reasons for Refusal dated Nov. 2, 2020", with English translation, 9 pgs.
"Japanese Application Serial No. 2018-32945, Response filed Feb. 2, 2021 to Notification of Reasons for Refusal dated Nov. 2, 2020", w/English Claims, 11 pgs.

* cited by examiner

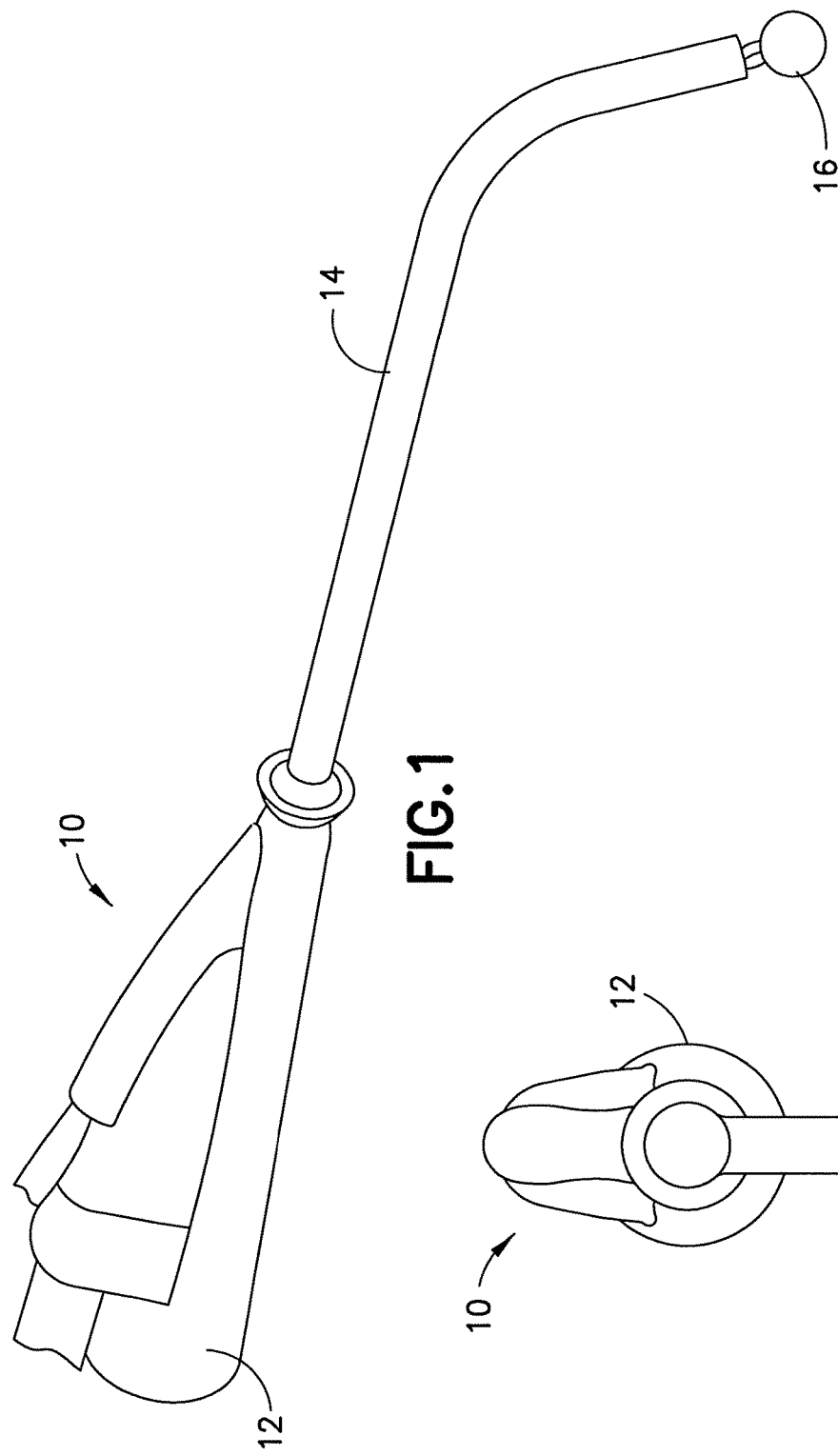
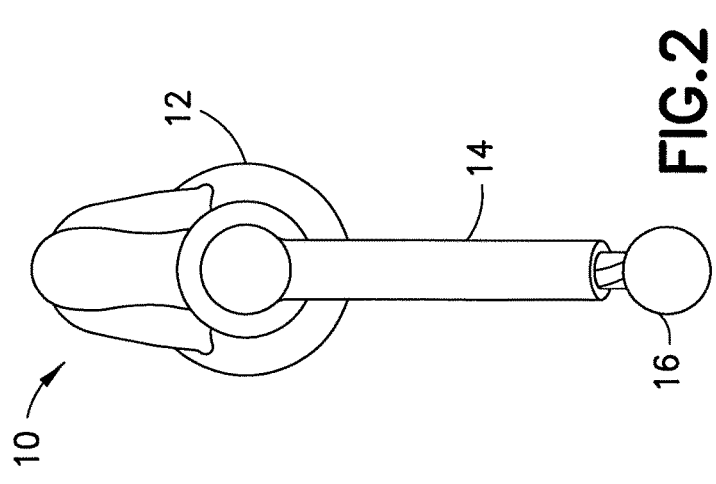

INTEGRATED SUCTION AND COOLING OF ANGLED BURR

CROSS REFERENCE TO RELATED APPLICATION

This is a continuation of co-pending U.S. application Ser. No. 15/464,492 filed Mar. 21, 2017 which is hereby incorporated by reference in its entirety.

BACKGROUND

Field of the Invention

The invention relates to an angled high speed burr, and more specifically relates to integrated suction and cooling for an angled high speed burr.

Brief Description of Prior Developments

Many of the conventional powered medical instruments/handpieces having angled burrs run at a speed up to 30,000 rpm from 15 degrees to 90 degrees angle of bend. Though it seems that this is a high speed, many surgeons desire a faster RPM to reduce the drilling time. Currently, in order to increase the speed of the drilling process in a frontal sinusotomy procedure for example, the surgeon has to provide increased hand pressure to excise the bone from the nasal crest. This tends to add fatigue to the surgeon and also raises a safety concern since an over pressure on a spinning burr can sometimes slide off and unintentionally damage adjacent bone tissues if not held firmly by the surgeon. Additionally, this could add more torque load to the motor and results in a temperature to rise on the handpiece.

Additionally, as burr outer sheath diameters become smaller, the suction path, internal or external, consequently becomes smaller thus causing clogging in the burrs' shaft internally or externally on the suction tube. This situation causes delays by having to de-clog the disposable burr in use and/or adds up cost to the procedure by having to replace the clogged burr.

Accordingly, as the conventional designs generally result in various limitations and disadvantages (as described above), there is a need to provide improved and reliable product configurations.

SUMMARY

In accordance with one aspect of the invention, a surgical device is disclosed. The surgical device includes a cutting burr, a flexible/deflectable shaft, an elongated fluted shaft, a sheath, and an outer tube. The cutting burr has a fluted extension. The flexible/deflectable shaft has a distal end and a proximal end, the distal end is configured to be connectable to the fluted extension of the cutting burr. The elongated fluted shaft is configured to be connectable to the proximal end of the flexible shaft. The sheath is configured to receive all or portion of the flexible shaft and the elongated fluted shaft. The outer tube is configured to receive the sheath such that there is enough space for fluid irrigation between the outer tube and the sheath.

In accordance with another aspect of the invention, a surgical device is disclosed. The surgical device includes a cutting burr, a flexible/deflectable shaft, an elongated fluted shaft, a sheath, an outer tube, and a housing. The cutting burr has a fluted extension. The flexible/deflectable shaft has a distal end and a proximal end, the distal end configured to be connectable to the fluted extension of the cutting burr. The elongated fluted shaft is configured to be connectable to the proximal end of the flexible shaft. The sheath is configured to be capable of receiving the connected flexible shaft and the elongated fluted shaft. The diameter of the sheath is greater than that of the elongated shaft or the fluted extension of the cutting burr to allow for fluid suction. The outer tube is configured to receive the sheath such that there is enough space between the outer tube and the sheath for fluid irrigation. The housing is configured to be connectable to the elongated shaft, the sheath, and the outer tube.

In accordance with another aspect of the invention, a surgical device is disclosed. The surgical device includes a cutting burr, a flexible/deflectable shaft, an elongated fluted shaft, a sheath, and an outer tube. The cutting burr has a head and an extended portion. The flexible/deflectable shaft has a distal end and a proximal end, the distal end configured to be fixedly connectable to the extended portion of the cutting burr. The elongated fluted shaft is configured to be fixedly connectable to the proximal end of the flexible shaft. The sheath is configured to receive the connected flexible shaft and the elongated fluted shaft, and all or a portion of the extended portion of the cutting burr. The diameter of the sheath is greater than that of the elongated shaft or the extended portion of the cutting burr to allow for fluid suction. The outer tube is configured to receive the sheath such that there is enough space for fluid irrigation between the outer tube and the sheath.

BRIEF DESCRIPTION OF THE DRAWINGS

The foregoing aspects and other features of the invention are explained in the following description, taken in connection with the accompanying drawings, wherein:

FIG. 1 is a perspective view of a disposable surgical burr attachment assembly incorporating features of the invention;

FIG. 2 is a front view of the disposable surgical burr attachment assembly shown in FIG. 1;

DETAILED DESCRIPTION

Figure 3:
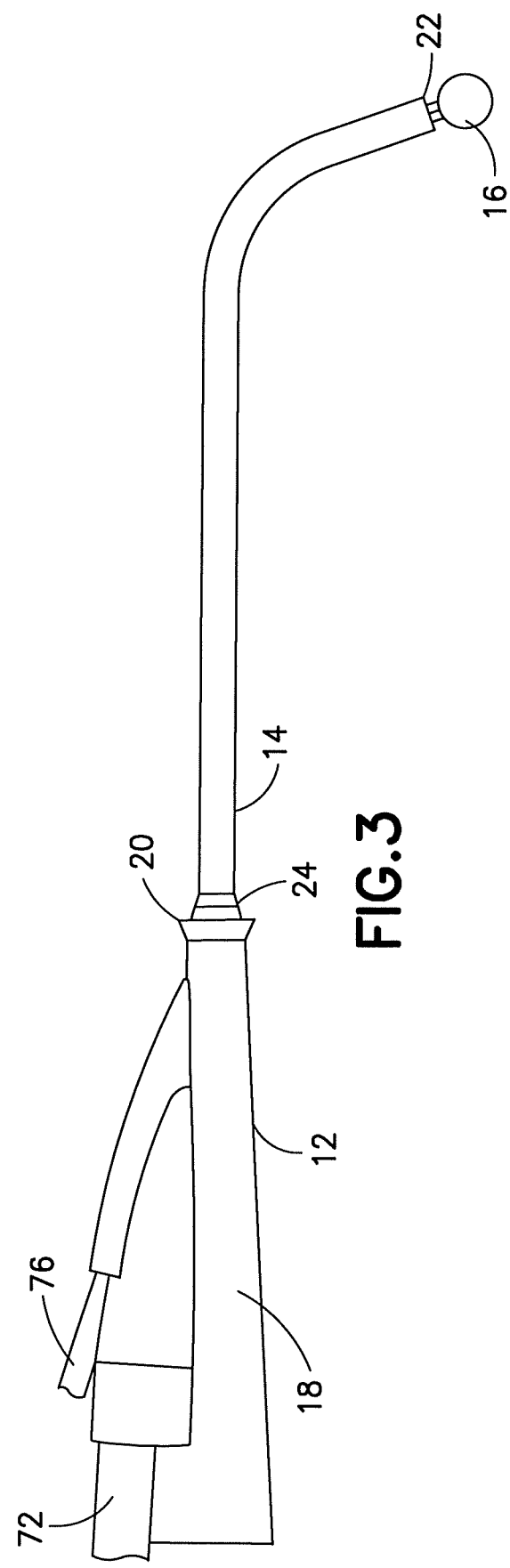
FIG. 3 is a side view of the disposable surgical burr attachment assembly shown in FIG. 1.

Referring to FIG. 1, there is shown a perspective view of a disposable surgical burr attachment assembly 10 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

The disposable surgical burr attachment assembly 10 (also shown in FIG. 2) includes a handpiece attachment portion 12, a flexible tube portion 14, and a rotating burr portion 16. Referring now also to FIG. 3, the handpiece attachment portion 12 includes a housing having an attachment hub 18 and a tube locking ring 20. The flexible tube portion 14 comprises a first end 22 and an opposite second end 24. The first (or distal) end 22 of the flexible tube portion 14 is connected to the rotating burr portion 16. The second (or proximal) end 24 of the flexible tube portion 14 is connected to the attachment hub 18 and secured to the handpiece attachment portion 12 by the tube locking ring 20. Additionally, the handpiece portion 10 is configured to be connected to suction tubing 72 and irrigation tubing 76.

Figure 4:
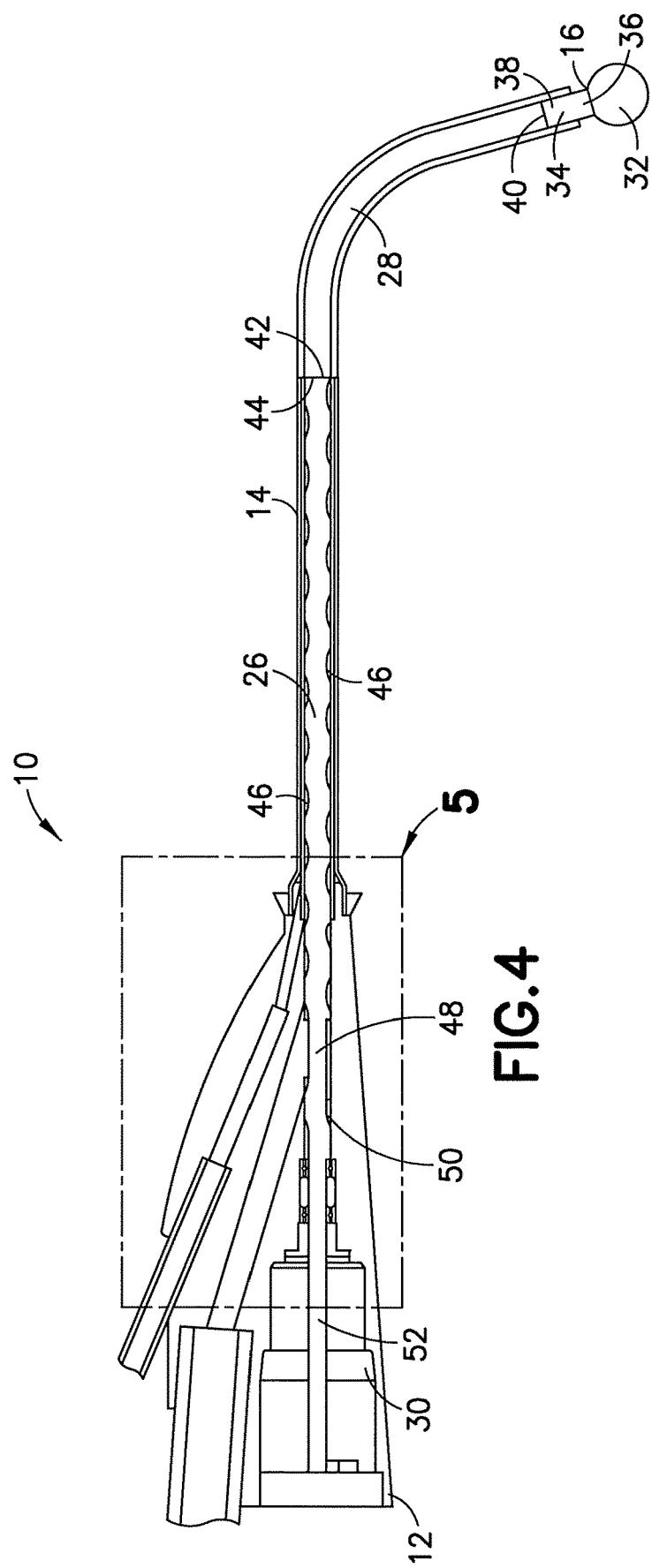
FIG. 4 is a partial section view of the disposable surgical burr attachment assembly shown in FIG. 1.

Referring now also to FIG. 4, illustrating a section view of the burr assembly 10, there is shown a fluted shaft 26 and a flexible shaft 28 extending between the cutting burr 16 and a shaft support 30 of the burr attachment assembly 10. The rotating burr portion (or cutting burr) 16 comprises a head portion (or burr) 32 and an extended portion (or burr tip) 34. The extended portion 34 comprises a neck section 36 at the head portion 32 and a shank section 38 at the flexible shaft 28. According to various exemplary embodiments, the head portion 32 and the extended portion 34 may be coupled together in any suitable fashion, such as a press fit or a slide fit with solder welding, for example. However in alternate embodiments the head portion 32 and the extended portion 34 may be integrally formed. Additionally, a first end 40 of the flexible shaft 28 is coupled to the extended portion 34 of the cutting burr 16 and a second end 42 of the flexible shaft 28 is coupled to the fluted shaft 26. According to various exemplary embodiments, one method of connecting these parts to the flexible shaft 28 is to drill a blind hole at the shank section 38 of the extended portion 34 and to drill a blind hole at an end 44 of the fluted shaft 28 and then insert the first end 40 of the flexible shaft 28 into the blind hole at the shank section 38 and insert the second end 42 of the flexible shaft 28 in the blind hole at the first end 44 of the fluted shaft 26 to provide a slide fit and then finishing off the coupling with silver solder welding to make permanent couplings between the fluted shaft 26, the flexible shaft 28, and the shank section 38 of the cutting burr 16. However, in alternate embodiments any suitable method of coupling the fluted shaft 26, the flexible shaft 28, and the shank section 38 of the cutting burr 16 may be provided.

The fluted shaft 26 and the flexible shaft 28 are sized and shaped to be rotatable within the flexible tube portion 14. The fluted shaft 26 may further comprise spiraled grooves on the outer surface of the shaft similar to the configuration of a drill bit. According to various exemplary embodiments, the spiraled grooves 46 between the first end 44 of the fluted shaft 26 the narrowed portion 48 of the shaft 26 may comprise a clockwise (CW) configuration, and the spiraled grooves 50 between the second end 52 of the fluted shaft 26 the narrowed portion 48 of the shaft 26 may comprise a counter clockwise (CCW) configuration. However in alternate embodiments, any suitable configurations for the spiraled grooves may be provided.

The bend angle of the flexible tube portion 14 is achieved by the flexible shaft 28. It should be noted that the flexible shaft 28 may be any suitable type of flexible/deflectable shaft which is configured to transmit rotary motion such as a flexible shaft manufactured by S.S. White Technologies Inc., for example. The configuration and flexibility of the shaft 28 to maintain the bend angle while rotating allows the burr to be angled from about 15° to about 90° with a minimum bend radius of ⅝"-1" while maintaining the ability to be spun by the high speed drill (HSD) handpiece 10.

Figure 5:
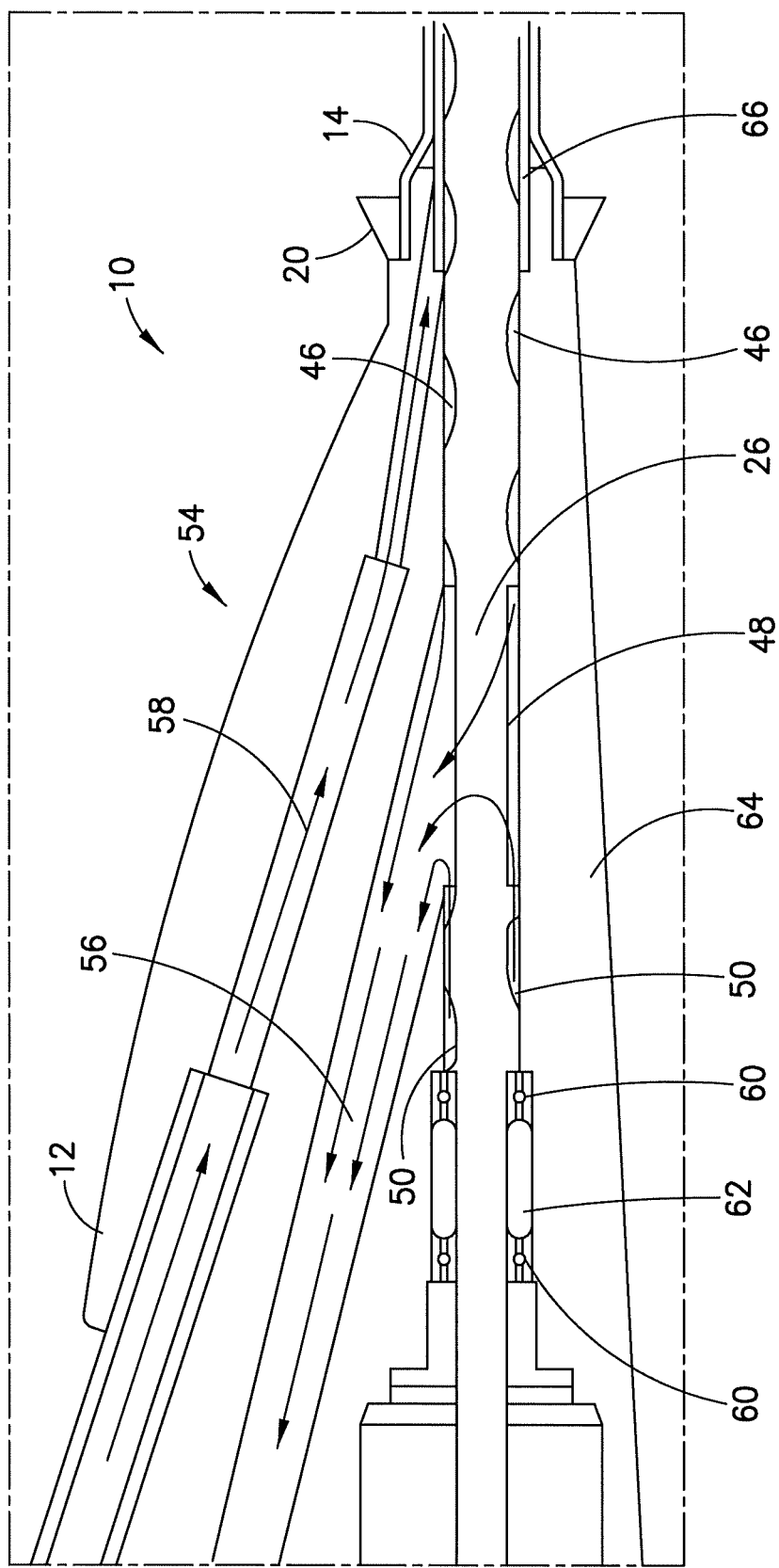
FIG. 5 is an enlarged section view of the designated portion of FIG. 4.

Referring now also to FIG. 5, there is shown an enlarged view of a portion of FIG. 4 wherein a Y-junction 54 of the handpiece portion 12 is illustrated. A portion of the Y-junction 54 is aligned with the narrowed portion 48 of the shaft 26 to provide a suction path 56. Another portion of the Y-junction 54 is aligned between the narrowed portion 48 of the shaft 26 and the first end 44 of the shaft 26 to provide an irrigation path 58. FIG. 5 also illustrates bearings 60 and a spacer 62 between the narrowed portion 48 of the shaft 26 and the second end 52 of the fluted shaft 26 (at an attachment hub section 64 of the handpiece portion 12) and a sheath 66 between the fluted shaft 26 and the flexible tube portion 14.

Figure 6:
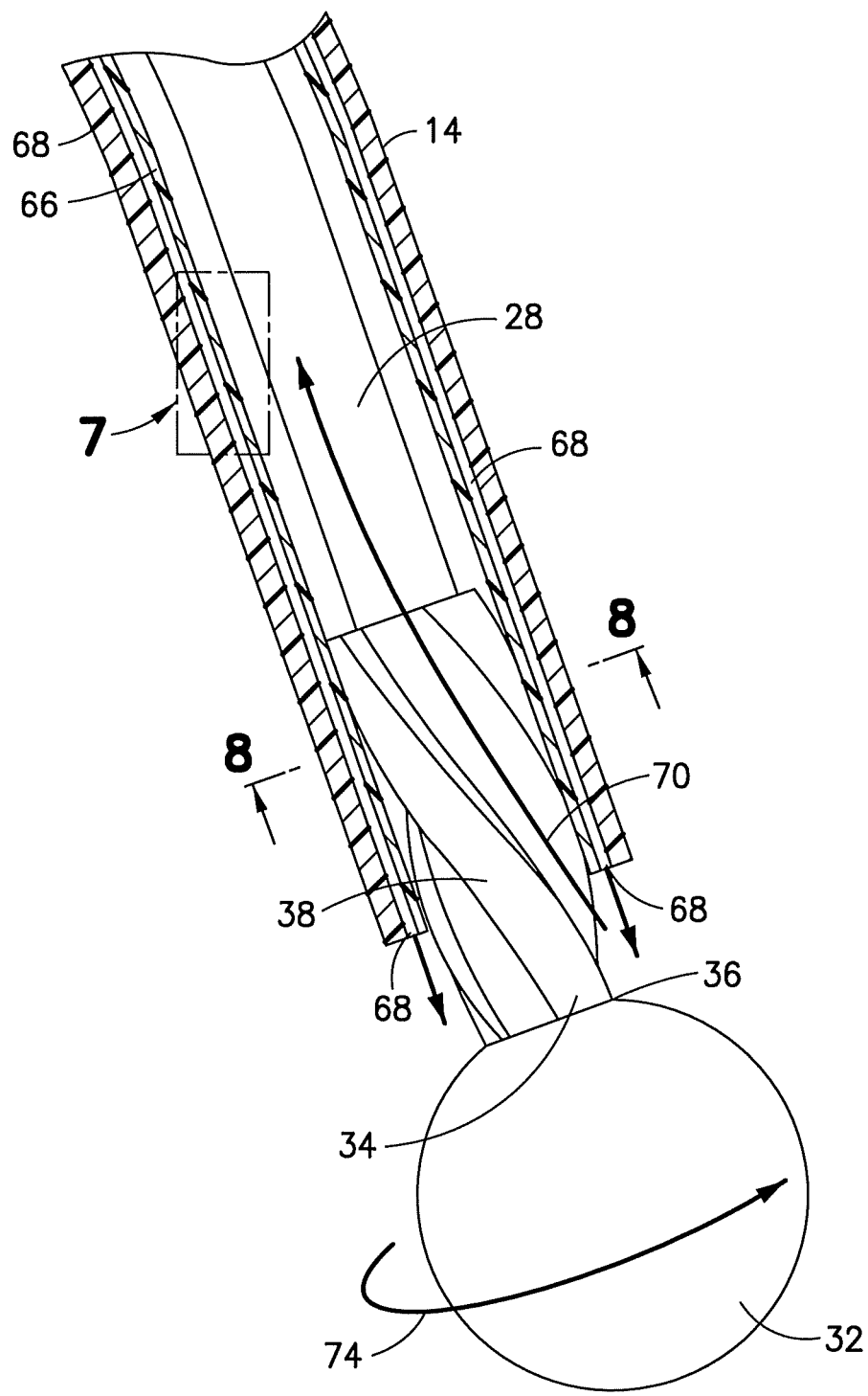
FIG. 6 is a partial section view of an end of a tube portion and rotating burr portion shown in FIG. 1.

Referring now also to FIG. 6, the sheath 66, which may be a metallic sheath for example, provides a tubular section which allows for different flow passages within the flexible tube portion 14. For example, a first flow passage (or irrigation flow passage) 68 is provided between the outer surface of the sheath 66 and the inner surface of the flexible tube portion 14. Additionally, a second flow passage (or suction flow passage) 70 is provided between the outer surface of the flexible shaft 28 and the inner surface of the sheath 66. The suction flow passage 70 is also provided between the outer surface of the extended portion 34 and the inner surface of the sheath 66 and between the outer surface of the fluted shaft 26 and the inner surface of the sheath 66.

During operation, the flexible shaft 28 rotates inside the outer sheath 66 as it extends through the bend angle of the flexible tube portion 14. At higher RPM speeds however, the contact friction between the inner wall of the outer sheath 66 and the flexible shaft 28 may cause heat to be generated. Various exemplary embodiments include the integrated irrigation line 68 where liquid can flow by the configuration of the flexible outer tube over the metallic outer sheath 66 with minimal clearance therebetween. Continuous irrigation of water or saline solution through this clearance between the flexible tube 14 and the metallic sheath 66 allows heat transfer to dissipate and prevent excessive rise in temperature. One advantage of this configuration is that the material of the flexible tube 14 also has the characteristic to expand when heated. It should be noted that the flexible tube 14 may be any suitable type of flexible tube such as a PVC flexible tube manufactured by Qosina Corporation, for example. This configuration provides for increased cooling flow as when any spot on the metallic sheath the gets hotter, it partially expands at that portion of the flexible tube allowing for more cooling fluid to pass through.

Figure 8:
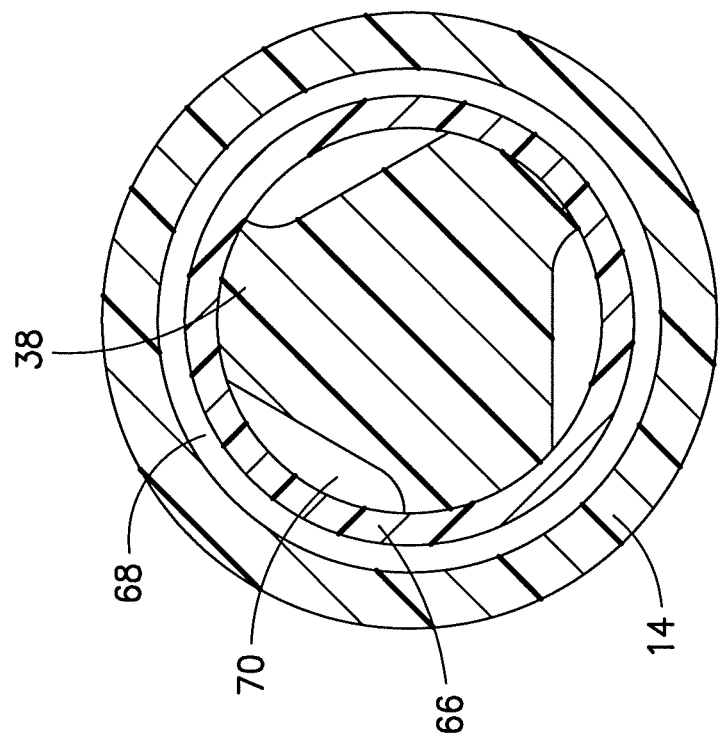
FIG. 8 is a section view of the designated portion of FIG. 6.
Figure 7:
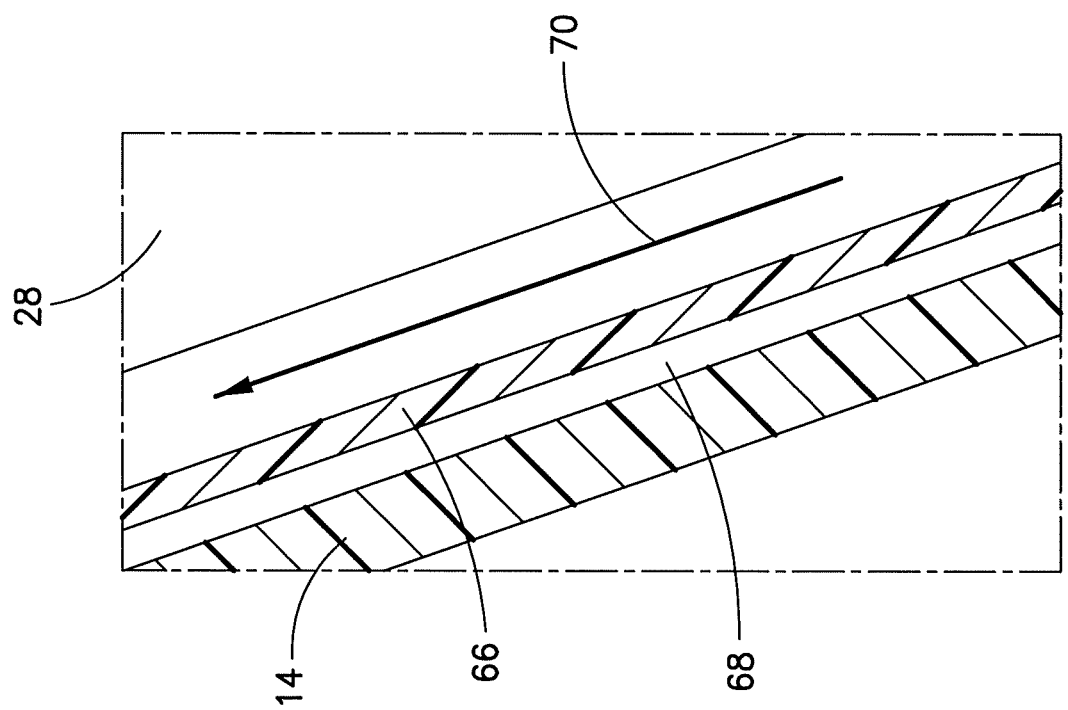
FIG. 7 is an enlarged section view of the designated portion of FIG. 6.

Referring now also to FIG. 7, which shows an enlarged view of a portion of FIG. 6, and FIG. 8 which shows a section view through the line 8-8 in FIG. 6, the suction flow passage 70 is provided through the passage inside the metallic outer sheath 66 from the fluted burr tip neck 36, and through the clearance (or concentric gap) between the flexible shaft 28 and the sheath 66 and then through the clearance (or concentric gap) between the fluted shaft 26 and the sheath 66 and further exits to the suction path 56 at the Y-junction 56 which leads to suction tubing 72 at the handpiece portion 12. Similar to the fluted shaft 26, the burr tip neck 36 and shank 38 may also comprise spiraled grooves on the outer surface of the neck 36 and shank 38 similar to the configuration of a drill bit. This suction feature facilitates debris evacuation and prevents clogging by further grinding of larger debris and channeling them backwards to these three clockwise flutes until it reaches the Y-junction 54. As noted above, the portion of the fluted shaft 26 between the second end 52 and the narrowed portion 48 (i.e. behind the Y-junction) may comprise counter clockwise (CCW) orientation of the spiraled grooves 50. This feature "pushes" the fluids and debris forward to the Y-junction 54 and helps prevent suction fluid from leaking behind the bearings 60 and spacer(s) 62. This feature could also eliminate the need of a dynamic seal abound the bearing which can cause additional unneeded load torque. According to various exemplary embodiments, the dimension of the concentric gaps (described above in relation to the suction flow passage) may be about 0.001 inches to about 0.06 inches (along a radius from centerline), with a preferred concentric gap of about 0.02 inches (along a radius from centerline).

Figure 9:
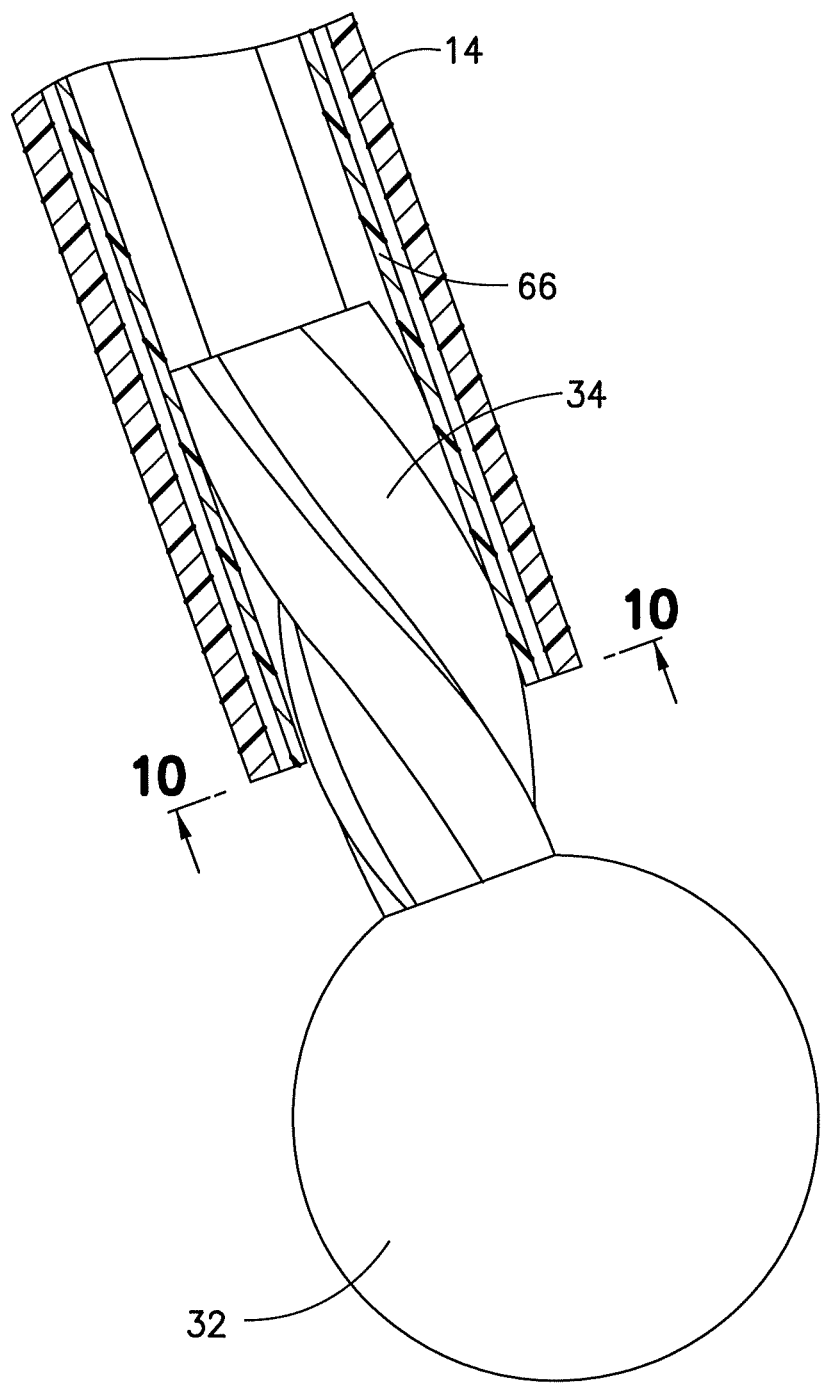
FIG. 9 is a partial section view of an end of a tube portion and rotating burr portion shown in FIG. 1.
Figure 10A:
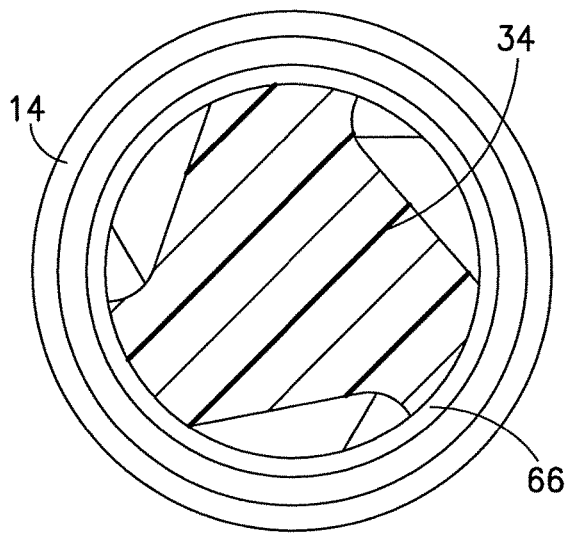
FIG. 10A shows an exemplary section view of the designated portion of FIG. 9.
Figure 10B:
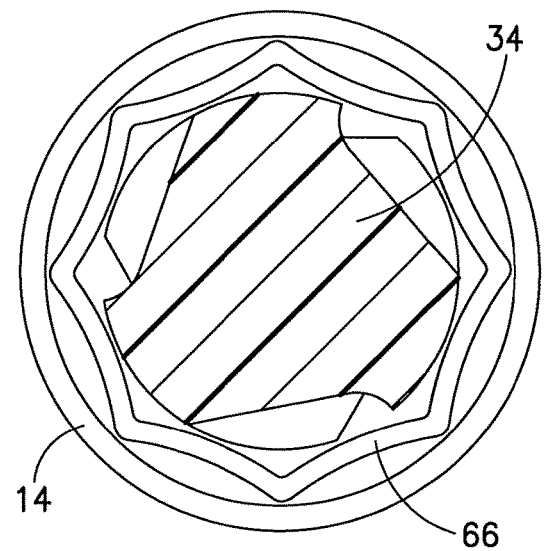
FIG. 10B shows another exemplary section view of the designated portion of FIG. 9.
Figure 10C:
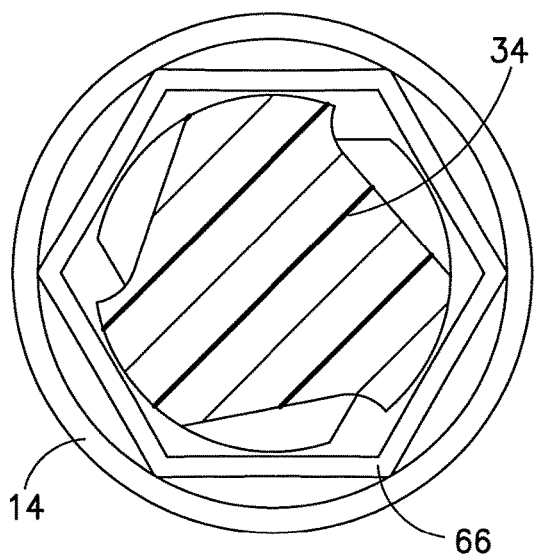
FIG. 10C shows another exemplary section view of the designated portion of FIG. 9.
Figure 10D:
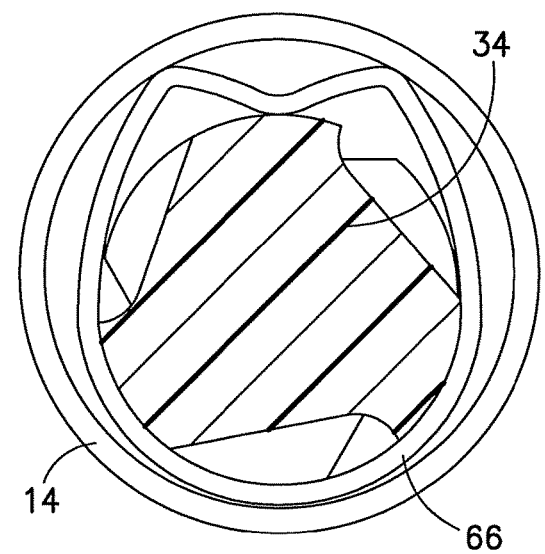
FIG. 10D shows another exemplary section view of the designated portion of FIG. 9.

FIGS. 6-8 also illustrate the irrigation/cooling flow passage 68 which provides for fluid to be directed to the burr tip 34 while the burr 16 is rotating 74 in operation. The irrigation flow passage 68 is in fluid communication with the irrigation path 58 (which is connected to irrigation tubing 76) and is provided through the clearance (or concentric gap) between the sheath 66 and the flexible tube portion 14 from the irrigation path 58 to the burr portion 16. Various exemplary embodiments provide for a state of high spray velocity in order to reach the burr tip and evenly spread to a specific area and not to be allowed to go back immediately under suction pressure. FIGS. 9, 10 further illustrate various possible nozzle option cross sections which vary the shape of the metallic outer sheath 66 within the flexible tube 14 (see portions A, B, C, D of FIG. 10 which may include a circular cross section, an octagonal cross section, a hexagonal cross section, a profiled cross section, or any other suitably shaped cross section shape). According to various exemplary embodiments, the dimension of the concentric gap (described above in relation to the irrigation flow passage) may be about 0.001 inches to about 0.06 inches (along a radius from centerline), with a preferred concentric gap of about 0.02 inches (along a radius from centerline).

Technical effects of any one or more of the exemplary embodiments provide significant advantages over conventional configurations having various manufacturing challenges since more small parts in the conventional designs need to be assembled together by welding the external suction line and the external irrigation line if not attaching additional clips to the disposable attachment.

Additional technical effects of any one or more of the exemplary embodiments provide for a high speed burr which can run at an RPM of at least 45K which is 50% than the maximum RPM currently offered in the market. This provides for the burr to cut faster without exerting excessive pressure to the bone tissue which minimizes, if not eliminates, burr sideways slips and slides. Additionally, this will allow the operating surgeon to focus more on the quality and precision of the cutting shape. Additional technical effects of any one or more of the exemplary embodiments also address the issues related to suction clogging and the cumbersome attachments for irrigation clips by having an integrated design to accommodate these features. Additional technical effects of any one or more of the exemplary embodiments also provide for multiple stock keeping units (SKUs) of disposable higher speed 45K RPM burrs with 15-90 degree bend angle with integrated suction and cooling/irrigation system.

Further technical effects of any one or more of the exemplary embodiments achieve higher RPM speeds with the flexible shaft that meets various diameter size and flexibility requirements, reduce the heat generated by friction at high RPM, and provide system integration of suction as well as irrigation to minimize clogging and to provide adequate lubrication to the burr in operation.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, a surgical device is disclosed. The surgical device comprises a cutting burr having a fluted extension; a flexible/deflectable shaft having a distal end and a proximal end, the distal end configured to be connectable to the fluted extension of the cutting burr; an elongated fluted shaft configured to be connectable to the proximal end of the flexible shaft; a sheath configured to receive all or portion of the flexible shaft and the elongated fluted shaft; and an outer tube configured to receive the sheath such that there is enough space for fluid irrigation between the outer tube and the sheath.

A surgical device as above, wherein the fluted extension comprises spiraled grooves.

A surgical device as above, wherein the fluted shaft comprises spiraled grooves.

A surgical device as above, wherein the sheath is between the fluted shaft and the outer tube.

A surgical device as above, wherein the sheath is between the fluted extension and the outer tube.

A surgical device as above, wherein the sheath is between the flexible shaft and the outer tube.

A surgical device as above, wherein the distal end is configured to be fixedly connectable to the fluted extension of the cutting burr.

A surgical device as above, wherein the elongated fluted shaft is configured to be fixedly connectable to the proximal end of the flexible shaft.

In another exemplary embodiment, a surgical device is disclosed. The surgical device comprises a cutting burr having a fluted extension; a flexible/deflectable shaft having a distal end and a proximal end, the distal end configured to be connectable to the fluted extension of the cutting burr; an elongated fluted shaft configured to be connectable to the proximal end of the flexible shaft; a sheath configured to be capable of receiving the connected flexible shaft and the elongated fluted shaft, wherein the diameter of the sheath is greater than that of the elongated shaft or the fluted extension of the cutting burr to allow for fluid suction; an outer tube configured to receive the sheath such that there is enough space between the outer tube and the sheath for fluid irrigation; and a housing configured to be connectable to the elongated shaft, the sheath, and the outer tube.

A surgical device as above, wherein the fluted extension comprises spiraled grooves.

A surgical device as above, wherein the fluted shaft comprises spiraled grooves.

A surgical device as above, wherein the sheath is between the fluted shaft and the outer tube.

A surgical device as above, wherein the sheath is between the fluted extension and the outer tube.

A surgical device as above, wherein the sheath is between the flexible shaft and the outer tube.

In another exemplary embodiment, a surgical device is disclosed. The surgical device comprises a cutting burr having a head and an extended portion; a flexible/deflectable shaft having a distal end and a proximal end, the distal end configured to be fixedly connectable to the extended portion of the cutting burr; an elongated fluted shaft configured to be fixedly connectable to the proximal end of the flexible shaft; a sheath configured to receive the connected flexible shaft and the elongated fluted shaft, and all or a portion of the extended portion of the cutting burr, wherein the diameter of the sheath is greater than that of the elongated shaft or the extended portion of the cutting burr to allow for fluid suction; and an outer tube configured to receive the sheath such that there is enough space for fluid irrigation between the outer tube and the sheath.

A surgical device as above, wherein the fluted extension comprises spiraled grooves.

A surgical device as above, wherein the fluted shaft comprises spiraled grooves.

A surgical device as above, wherein the sheath is between the fluted shaft and the outer tube.

A surgical device as above, wherein the sheath is between the fluted extension and the outer tube.

A surgical device as above, wherein the sheath is between the flexible shaft and the outer tube.

It should be understood that components of the invention can be operationally coupled or connected and that any number or combination of intervening elements can exist (including no intervening elements). The connections can be direct or indirect and additionally there can merely be a functional relationship between components.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A surgical device comprising:
   a cutting burr having a head and an extended portion;
   a flexible shaft having a distal end and a proximal end, the distal end configured to be connectable to the extended portion of the cutting burr;
   an elongated fluted shaft configured to be connectable to the proximal end of the flexible shaft, wherein at least a majority of the flexible shaft is between the cutting burr and the elongated fluted shaft; and
   a sheath configured to receive all or a portion of the flexible shaft and the elongated fluted shaft.

2. The surgical device of claim 1, further comprising:
   an outer tube configured to receive the sheath such that there is space for fluid irrigation between the outer tube and the sheath.

3. The surgical device of claim 2 wherein the sheath is between the elongated fluted shaft and the outer tube.

4. The surgical device of claim 2 wherein the sheath is between the extended portion and the outer tube.

5. The surgical device of claim 2 wherein the sheath is between the flexible shaft and the outer tube.

6. The surgical device of claim 2, further comprising:
   a housing configured to be connectable to the elongated shaft, the sheath, and the outer tube.

7. The surgical device of claim 1 wherein the extended portion comprises spiraled grooves.

8. The surgical device of claim 1 wherein the elongated fluted shaft comprises spiraled grooves.

9. The surgical device of claim 1 wherein the distal end is configured to be fixedly connectable to the extended portion of the cutting burr.

10. The surgical device of claim 1 wherein the elongated fluted shaft is configured to be fixedly connectable to the proximal end of the flexible shaft.

11. The surgical device of claim 1 wherein the extended portion is fluted.

12. The surgical device of claim 1 wherein a diameter of the sheath is greater than a diameter of the elongated fluted shaft or a diameter of the extended portion of the cutting burr to allow for fluid suction.

13. A surgical device comprising:
    a cutting burr comprising a head and an extended portion;
    a flexible shaft comprising a distal end and a proximal end, wherein the distal end is connected to the extended portion of the cutting burr;
    an elongated fluted shaft connected to the proximal end of the flexible shaft, wherein a majority of the flexible shaft is located between the cutting burr and the elongated fluted shaft; and
    a sheath having at least a portion of the flexible shaft and a portion of the elongated fluted shaft located therein.

14. The surgical device of claim 13, further comprising:
    an outer tube configured to receive the sheath such that there is space for fluid irrigation between the outer tube and the sheath.

15. The surgical device of claim 14 wherein the sheath is between the elongated fluted shaft and the outer tube.

16. The surgical device of claim 14 wherein the sheath is between the extended portion and the outer tube.

17. The surgical device of claim 14 wherein the sheath is between the flexible shaft and the outer tube.

18. The surgical device of claim 14, further comprising:
    a housing configured to be connectable to the elongated shaft, the sheath, and the outer tube.

19. The surgical device of claim 13 wherein the extended portion comprises spiraled grooves.

20. A surgical device comprising:
    a cutting burr comprising a head and an extended portion;
    a flexible shaft comprising a distal end and a proximal end, wherein the distal end is configured to be connected to the extended portion of the cutting burr;
    an elongated fluted shaft, wherein the elongated fluted shaft is configured to be connected to the proximal end of the flexible shaft, and wherein a majority of the flexible shaft is configured to be located between the cutting burr and the elongated fluted shaft; and
    a sheath, wherein the sheath is configured to have at least a portion of the flexible shaft and a portion of the elongated fluted shaft located therein.

* * * * *